US011471322B1

(12) United States Patent
Bright et al.

(10) Patent No.: US 11,471,322 B1
(45) Date of Patent: Oct. 18, 2022

(54) SYSTEMS AND METHODS OF COOLING A PATIENT

(71) Applicant: CRYO CAP LLC, Manassas, VA (US)

(72) Inventors: Tony Bright, Manassas, VA (US); Hamza Arman Lateef, Manassas, VA (US); Gabriel Ralston, Manassas, VA (US); Solomon Ralston, Manassas, VA (US)

(73) Assignee: CRYO CAP LLC, Manassas, VA (US)

( * ) Notice: Subject to any disclaimer, the term of this patent is extended or adjusted under 35 U.S.C. 154(b) by 0 days.

(21) Appl. No.: 17/659,818

(22) Filed: Apr. 19, 2022

Related U.S. Application Data

(60) Provisional application No. 63/318,303, filed on Mar. 9, 2022.

(51) Int. Cl.
  *G16H 10/20* (2018.01)
  *A61F 7/00* (2006.01)
  *G16H 20/30* (2018.01)
  *G16H 50/20* (2018.01)

(52) U.S. Cl.
  CPC ........... *A61F 7/0085* (2013.01); *G16H 10/20* (2018.01); *G16H 20/30* (2018.01); *G16H 50/20* (2018.01); *A61F 2007/0002* (2013.01); *A61F 2007/0056* (2013.01)

(58) Field of Classification Search
  CPC ............ A61F 7/0085; A61F 2007/0002; A61F 2007/0056; G16H 20/30; G16H 50/20; G16H 10/20
  See application file for complete search history.

(56) References Cited

U.S. PATENT DOCUMENTS

| 4,172,495 A | 10/1979 | Zebuhr et al. |
| 5,913,885 A * | 6/1999 | Klatz ................. A61F 7/10 607/104 |
| 6,277,143 B1 | 8/2001 | Klatz et al. |

(Continued)

OTHER PUBLICATIONS

Committee on Sports-Related Concussions in Youth; Board on Children, Youth, and Families; Institute of Medicine; National Research Council; Graham R, Rivara FP, Ford MA, et al., editors. Sports-Related Concussions in Youth: Improving the Science, Changing the Culture. Washington (DC): National Academies Press (US); Feb. 4, 2014. Appendix C, Clinical Evaluation Tools. Available from: https://www.ncbi.nlm.nih.gov/books/NBK185341/ (356 pages, in English).

(Continued)

*Primary Examiner* — Tigist S Demie
(74) *Attorney, Agent, or Firm* — Book McAndrews, PLLC

(57) ABSTRACT

A method, including receiving diagnostic information, relating to a potential traumatic brain injury of a person; based on the received diagnostic information, determining a Glascow Coma Scale for the person; upon determining that the Glascow Coma Scale is above a threshold value, instructing use of a cooling system to manage a temperature of the person's head, wherein the cooling system includes: an insulated cap having one or more fluid conduits extending through the cap; a cooling control unit, a fluid line disposed between the cap and the cooling unit that tethers to cap and the cooling unit to one another; and one or more temperatures sensors configured to measure a temperature of the person's head.

10 Claims, 20 Drawing Sheets

(56) References Cited

U.S. PATENT DOCUMENTS

| | | | |
|---|---|---|---|
| 7,052,509 B2* | 5/2006 | Lennox | A61F 7/0085 |
| | | | 607/104 |
| 8,136,169 B2 | 3/2012 | Taylor | |
| 9,770,061 B2* | 9/2017 | Sansone | A42B 3/00 |
| 9,999,270 B2 | 6/2018 | Washington | |
| 10,342,696 B2* | 7/2019 | Rand | A61F 7/106 |
| 10,765,166 B2 | 9/2020 | Krishnan | |
| 2002/0103520 A1* | 8/2002 | Latham | A61F 7/10 |
| | | | 607/108 |

OTHER PUBLICATIONS

Lovell, Mark R., et al. "Neuropsychological assessment of the college football player." The Journal of head trauma rehabilitation 13.2 (1998): 9-26. (18 pages, in English).

Johnson WD, et al. Traumatic brain injury: a global challenge. Lancet Neurol. 2017;16:949-950. (2 pages, in English).

Miyauchi, Takashi, et al. "Evidence for the therapeutic efficacy of either mild hypothermia or oxygen radical scavengers after repetitive mild traumatic brain injury." Journal of neurotrauma 31.8 (2014): 773-781. (9 pages, in English).

\* cited by examiner

SYSTEMS AND METHODS OF COOLING A PATIENT

CROSS-REFERENCE TO RELATED APPLICATION

This application claims priority to US Provisional Patent Application No. 63/318,303, filed on Mar. 9, 2022, which is incorporated by reference herein in its entirety.

FIELD OF THE DISCLOSURE

Various embodiments of the present disclosure pertain generally to devices and methods for managing and/or treating traumatic brain injuries. More specifically, particular embodiments of the present disclosure relate to systems and methods for cooling to the head of a person diagnosed with a traumatic brain injury.

BACKGROUND

Traumatic brain injuries (TBI) are a major public health concern and a leading international cause of morbidity and mortality. It is now recognized that recurrent episodes of even mild TBI or concussions in contact sports may lead to neurodegenerative changes and culminate in a devastating condition called Chronic Traumatic Encephalopathy (CTE). CTE may be related to the buildup of an abnormal form of a protein (tau), in the brain, in the form of neurofibrillary tangles such as those found in Alzheimer's Disease.

Despite the well-recognized and devastating impact of TBI, no effective strategy exists to treat such disorders or to decrease the risk of long-term neurologic consequences. Primary brain injuries result from the direct mechanical trauma to brain cells at the time of initial impact. Secondary brain injuries may be caused by a series of biochemical events that occur after the initial impact and evolve over time. There may be a delay between the initial impact and secondary brain injuries.

SUMMARY OF THE DISCLOSURE

A method, including: receiving diagnostic information, using a mobile application, relating to a potential traumatic brain injury of a person, wherein receiving diagnostic information includes receiving answers to a questionnaire relating to the person, wherein the questionnaire includes a series of questions relating to the potential traumatic brain injury; based on the received diagnostic information, determining a Glascow Coma Scale for the person; upon determining that the Glascow Coma Scale is above a threshold value, instructing use of a cooling system to manage a temperature of the person's head, wherein the cooling system includes: an insulated cap having one or more fluid conduits extending through the cap; a cooling control unit, wherein the cooling control unit include a housing, a cooling assembly, a power source, a coolant pump configured to circulate coolant through the cooling system, a controller configured to control the coolant pump, and a converter; wherein the cooling assembly includes one or more cooling blocks through which coolant is configured to flow, a heat sink, and a thermoelectric cooler, wherein the cooler assembly is configured to remove heat from coolant flowing there through; a fluid line disposed between the cap and the cooling unit that tethers to cap and the cooling unit to one another; one or more temperatures sensors configured to measure a temperature of the person's head, wherein the one or more temperature sensors are coupled to the cap so as to contact a forehead or temple of the person when the cap is worn; the method further including: after the cap has been placed on a head of the person, operating the cooling system to flow liquid coolant through the cooling system to perform selective cerebral hypothermia to limit an extent of brain injury to the person; after the one or more temperature sensors have been placed in contact with the forehead or temple of the person, receiving measured temperature from the one or more temperature sensors; when the received measured temperature is below a low temperature threshold, ceasing the flow of coolant through cooling system; after cessation of use of the cooling system, sending an instruction to submit answers to additional questions, through the mobile application, after lapse of at least one day from cessation of use of the cooling system, wherein the additional questions relate to the potential traumatic brain injury of the person; and after lapse of at least one day from cessation of use of the cooling system, receiving the answers to the additional questions through the mobile application.

A method, including: receiving diagnostic information, using a mobile application, relating to a potential traumatic brain injury of a person, wherein receiving diagnostic information includes receiving answers to a questionnaire relating to the person, wherein the questionnaire includes a series of questions relating to the potential traumatic brain injury; based on the received diagnostic information, determining a Glascow Coma Scale for the person; upon determining that the Glascow Coma Scale is above a threshold value, instructing use of a cooling system to manage a temperature of the person's head, wherein the cooling system includes: an insulated cap having one or more fluid conduits extending through the cap; a cooling control unit, wherein the cooling control unit include a housing, a cooling assembly, a power source, a coolant pump configured to circulate coolant through the cooling system, a controller configured to control the coolant pump, and a converter, wherein the cooling assembly includes one or more cooling blocks through which coolant is configured to flow, a heat sink, and a thermoelectric cooler, wherein the cooler assembly is configured to remove heat from coolant flowing therethrough; a fluid line disposed between the cap and the cooling unit that tethers to cap and the cooling unit to one another; one or more temperature sensors configured to measure a temperature of the person's head, wherein the one or more temperature sensors are coupled to the cap so as to contact a forehead or temple of the person when the cap is worn; the method further including: after the cap has been placed on a head of the person, operating the cooling system to flow liquid coolant through the cooling system to perform selective cerebral hypothermia to limit an extent of brain injury to the person; after the one or more temperature sensors have been placed in contact with the forehead or temple of the person, receiving measured temperature from the one or more temperature sensors; when the received measured temperature is below a low temperature threshold, ceasing the flow of coolant through cooling system; after cessation of use of the cooling system, sending an instruction to submit answers to additional questions, through the mobile application, after lapse of at least one day from cessation of use of the cooling system, wherein the additional questions relate to the potential traumatic brain injury of the person; and after lapse of at least one day from cessation of use of the cooling system, receiving the answers to the additional questions through the mobile application.

Wherein the cap is a helmet. Wherein the one or more fluid conduits are embedded within the cap. Wherein the control unit is configured to prevent use of the cooling system when the determined Glascow Coma Scale is below the threshold. Wherein, when the measure temperature rises above the low temperature threshold, re-initiating a flow of coolant through the cooling system to withdraw heat from the head of the person. Wherein the low temperature threshold is 35 degrees Celsius. Wherein receiving the diagnostic information occurs within ten minutes of an event causing the traumatic brain injury. The method further including receiving measured temperature of the person's head for at least ten minutes after cessation of flow of coolant through the coolant system.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the present disclosure, examples of which are illustrated in the accompanying drawings. Wherever possible, the same reference numbers will be used throughout the drawings to refer to the same or like parts. In the discussion that follows, terms "about," "approximately," "substantially," and the like, when used in describing a numerical value, denote a variation of +/−10% of that value, unless specified otherwise.

Figure 1:
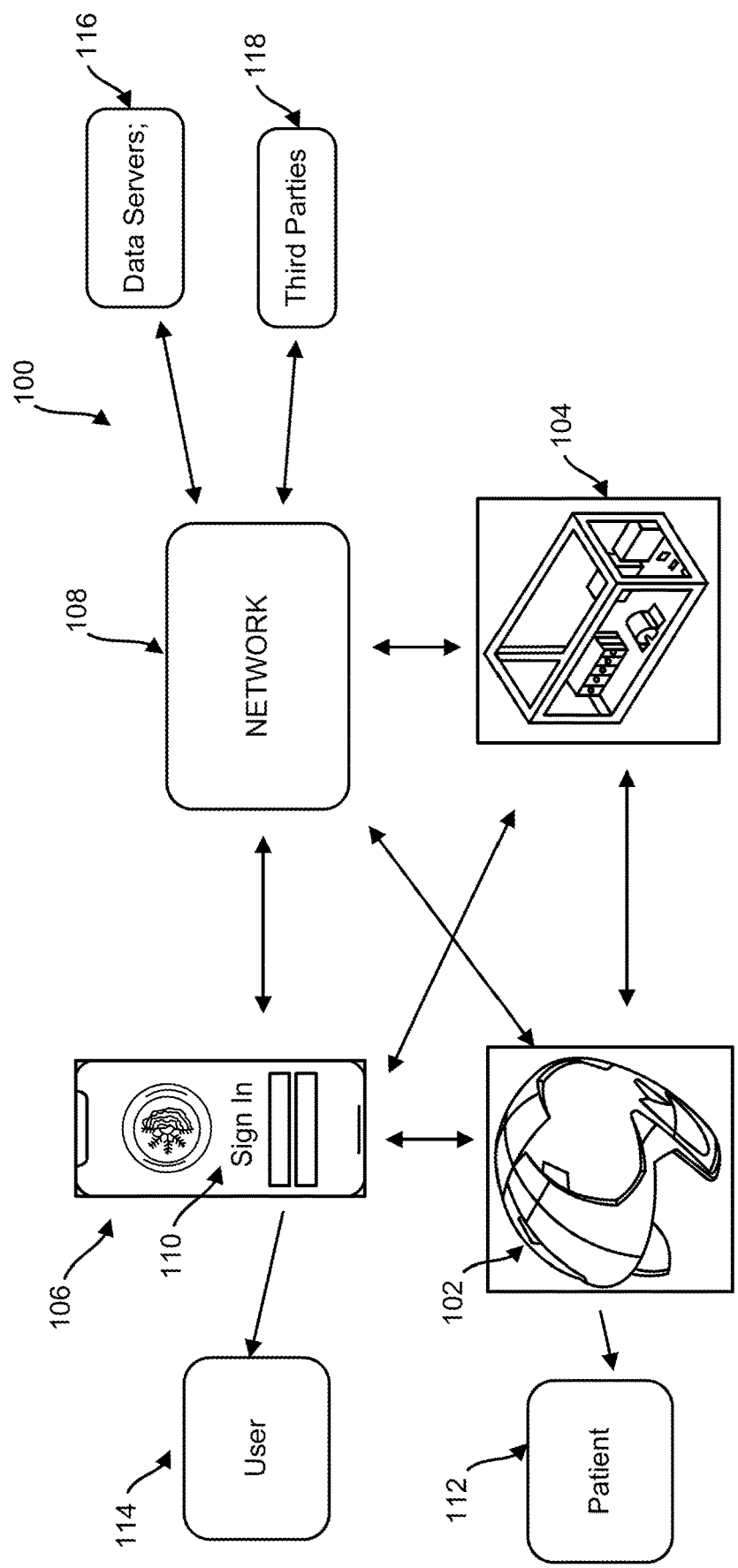
FIG. 1 is a schematic illustration of a cooling system, according to an example of the present disclosure.

FIG. 1 is a block diagram of a cooling system 100, according to an example of the present disclosure. A user 114 (e.g., doctor, athletic director, parent, student, athlete, parent, etc.) having an electronic device 106, such as a mobile device, computer, medical device, or any other electronic device configured to access an electronic network 108, such as the internet, may communicate with or otherwise access a mobile application 110 that is connected with a cooling cap 102 and a cooling control unit 104. In some examples, network 108 may include wireless or wired links, such as mobile telephone networks, Wi-Fi, LANs, WANs, Bluetooth, near-field communication (NFC), or other suitable forms of network communication. Multiple electronic devices 106 may be configured to access electronic network 108. A user 114 may access the mobile application 110 with a single account linked to multiple electronic devices 106 (e.g., via one or more of a mobile phone, a tablet, and a laptop computer). Electronic device 106 also may include, but is not limited to, mobile health devices, a desktop computer or workstation, a laptop computer, a mobile handset, a personal digital assistant (PDA), a cellular telephone, a network appliance, a smart phone, a smart watch, an enhanced general packet radio service (EGPRS) mobile phone, a media player, a navigation device, a game console, a set-top box, a biometric sensing device with communication capabilities, a smart TV, or any combination of these or other types of computing devices having at least one processor, a local memory, a display (e.g., a monitor or touchscreen display), one or more user input devices, and a network communication interface. The electronic device 106 may include any type or combination of input/output devices, such as a display monitor, keyboard, touchpad, accelerometer, gyroscope, mouse, touchscreen, camera, a projector, a touch panel, a pointing device, a scrolling device, a button, a switch, a motion sensor, an audio sensor, a pressure sensor, a thermal sensor, and/or microphone. Electronic devices 106 may be able to communicate with each other by any suitable wired or wireless means (e.g., via Wi-Fi, radio frequency (RF), infrared (IR), Bluetooth, Near Field Communication, or any other suitable means) to send and receive information.

The mobile application 110 may be in communication with other entities or networks to send and receive information. In some examples, the mobile application 110 may communicate with a cooling cap 102 and a cooling control unit 104. The mobile application 110 may be utilized by a user 114, such as a trainer, to help determine whether a person suspected of having a TBI should be approved to proceed with the use of a cooling cap 102 and cooling control unit 104. For example, mobile application 110 may help determine the Glascow Coma Scale (GCS) score of a second individual/patient 112 who may have had a recent brain injury. The mobile application 110 may include a series of questions or a questionnaire meant to determine the severity of the TBI (e.g. concussion) of patient 112 and to provide a GSC score and diagnostics. The mobile application 110 may provide simple and direct questions for a user 114 to ask a patient 112 about the patient's 112 physical and mental functioning. In one embodiment, the GCS measures and scores the following functions: Eye Opening (E) (4=spontaneous, 3=to sound, 2=to pressure, 1=none), Verbal Response (V) (5=orientated, 4=confused, 3=words, but not coherent, 2=sounds, but no words, 1=none), and Motor Response (M) (6=obeys command, 5=localizing, 4=normal flexion, 3=abnormal flexion, 2=extension, 1=none). A user 114 may then enter answers to the questionnaire within the mobile application 110. The mobile application 110 may then record all answers to the questionnaire and classify the brain injury, displaying and providing an individual's GSC score in the process. The GCS score may classify brain injuries as severe (GCS of 8 or less), moderate (GCS of 9-12) or mild (GCS of 13-15). The mobile application 110 may be able to export the data and classification to other devices or third parties 118.

The cooling system 100 may then access decision models that are stored in a data server 116 and accessed through the network 108. Alternatively, the decision models may be saved locally on the mobile application 110. The decision models may be used for processing by one or more of the electronic devices 106. The cooling system 100 may then analyze the GSC score and classification utilizing decision models to determine whether the cooling cap 102 should be applied to the patient 112. In one embodiment, the system 100 may determine that the cooling cap 102 is necessary for a patient 112 if the patient 112 receives a score at or above a minimum threshold, e.g. a GSC score between 12-14.

If the cooling cap 102 is necessary, the mobile application 110 may instruct the user 114 to initiate a therapy using the cooling cap 102 and cooling control unit 104. . The cooling cap 102, once placed on a patient's 112 head, may then receive coolant from a cooling control unit 104 that is in fluid communication with the cooling cap 102. The cooling cap 102 may also record the temperature of the patient 112 who is wearing the cooling cap 102. The mobile application 110 may record how long coolant has been provided to a patient 112 (i.e., recording the length of providing coolant and recording the overall length of treatment). In one embodiment, the cooling cap 102 may stop providing coolant and instruct patient 112 to remove the cooling cap 102 after a set period of time. In another embodiment, the cooling cap 102 may stop providing coolant to a patient 112 once the patient's 112 measured temperature has dropped under a lower threshold. In one embodiment, the lower threshold may be about 35 degrees Celsius, or another suitable threshold value. The cooling cap 102, may stay on the patient 112 and continue to monitor the patient's 112 temperature even after active cooling is paused or stopped. The cooling cap 102 may provide further coolant if the patient's 112 temperature raises to an unacceptable upper threshold after the cooling cap 102 has stopped cooling the patient 112. In one embodiment, the upper threshold may be about 37 degrees Celsius. The system 100 described herein may provide a benefit to a patient 112 by potentially reducing secondary brain injuries, e.g., that would have occurred in the absence of using any cooling treatment.

A user 114 of the mobile application 110, may be prompted and/or instructed to continue to answer questions provided by the mobile application 110 in the following weeks after the initial injury. The system 100 may record and track the data and answers future questions provided by the mobile application 110. This information may then be provided to third parties 118 later or in real time. In one embodiment, the system 100 may develop a recovery plan for patient 112 based on the data received.

The data servers 116, may be responsible for saving all data collected for each patient 112. The mobile application 110, may allow for a user 114 or third party to access collected data for each patient 112. This data may be utilized by patients 112, users 114, medical staff, and divisions such as school boards to access past information on an patient's 112 injuries.

Figure 2:
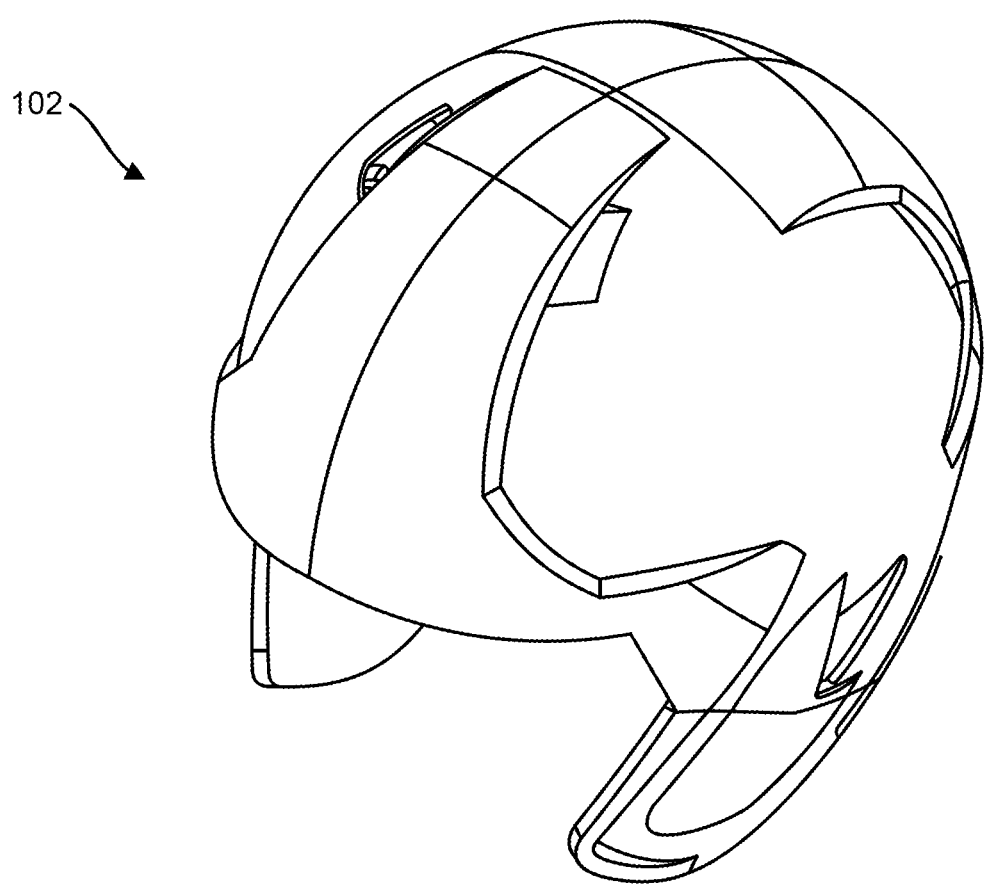
FIG. 2 depicts a perspective view of a cooling cap.

FIG. 2 depicts one embodiment of a cooling cap 102. The cooling cap 102 may be any type of wearable head device that may be worn by a patient 112 such as a helmet, cap, or headgear. The cooling cap 102, may have the ability to cool a user's 112 head by providing a coolant flow through coolant channels 204 (shown in FIG. 4). By delivering coolant, e.g., cerebral hypothermia, the system 100 may limit the extent of a brain injury and improve the long term cognitive outcomes of a patient 112 who utilizes the cooling system 100 after experiencing a TBI. The cooling cap 102 may receive coolant from a cooling control unit 104.

Figure 3:
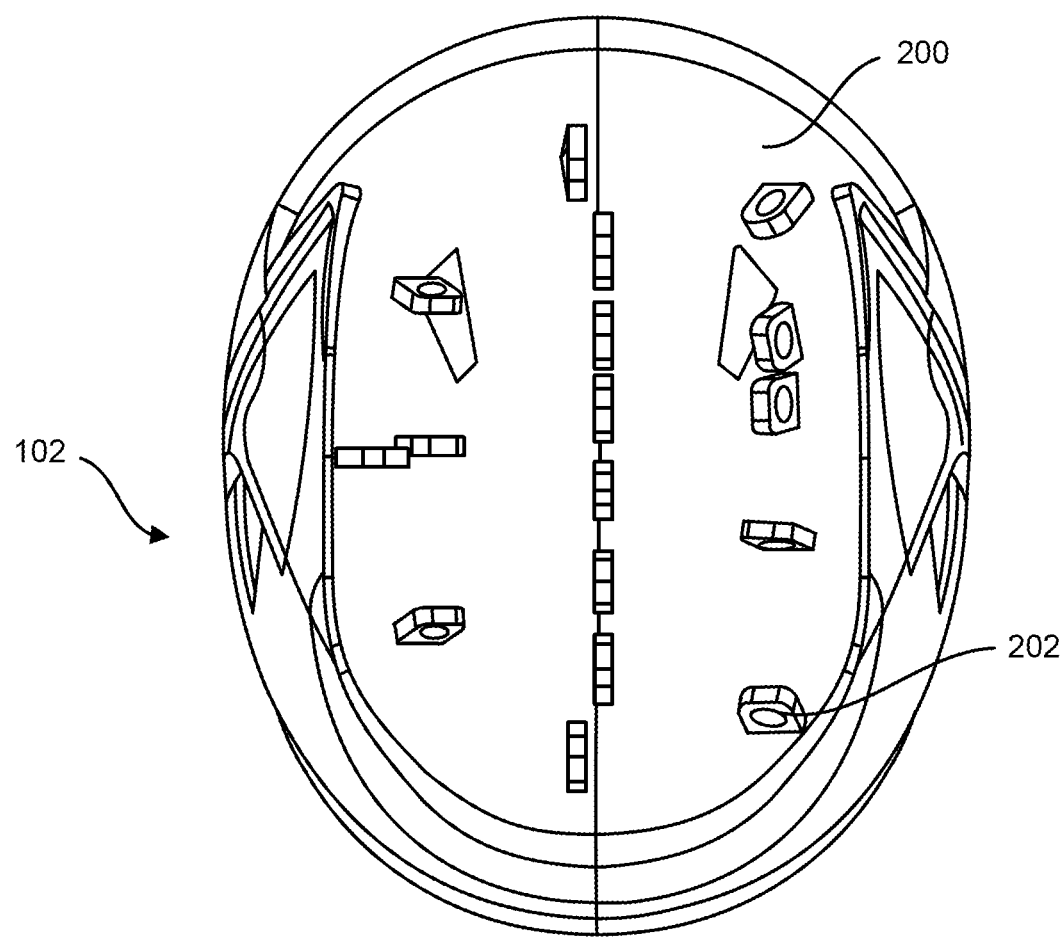
FIG. 3 depicts a bottom view of a cooling cap.

FIG. 3 depicts a perspective bottom view of the cooling cap 102. The cooling cap 102 may have an interior surface 200 that lines the inside of the cooling cap 102. The interior surface 200 may have padding including a fabric optimized for moisture wicking and easy drying. The cooling cap 102 may further include pneumatic layers of insulation. The interior surface 200 may have cooling tube clamps 202 that have the ability to hold a cooling tubes/channels 204 in place. The clamps 202 may consist of any device capable of holding a coolant tube/channel 204 such as: velcro, clamps, or any feasible attachment mechanism. In some embodiments, the clamp 202 may be molded to the cooling cap 102. In another embodiment, the clamps 202 may be clipped into the cooling cap 102 or otherwise removeably secured to. The clamps 202 and cooling tubes/channel 204 may be located within the interior surface 200 of the cooling cap 102.

Figure 4:
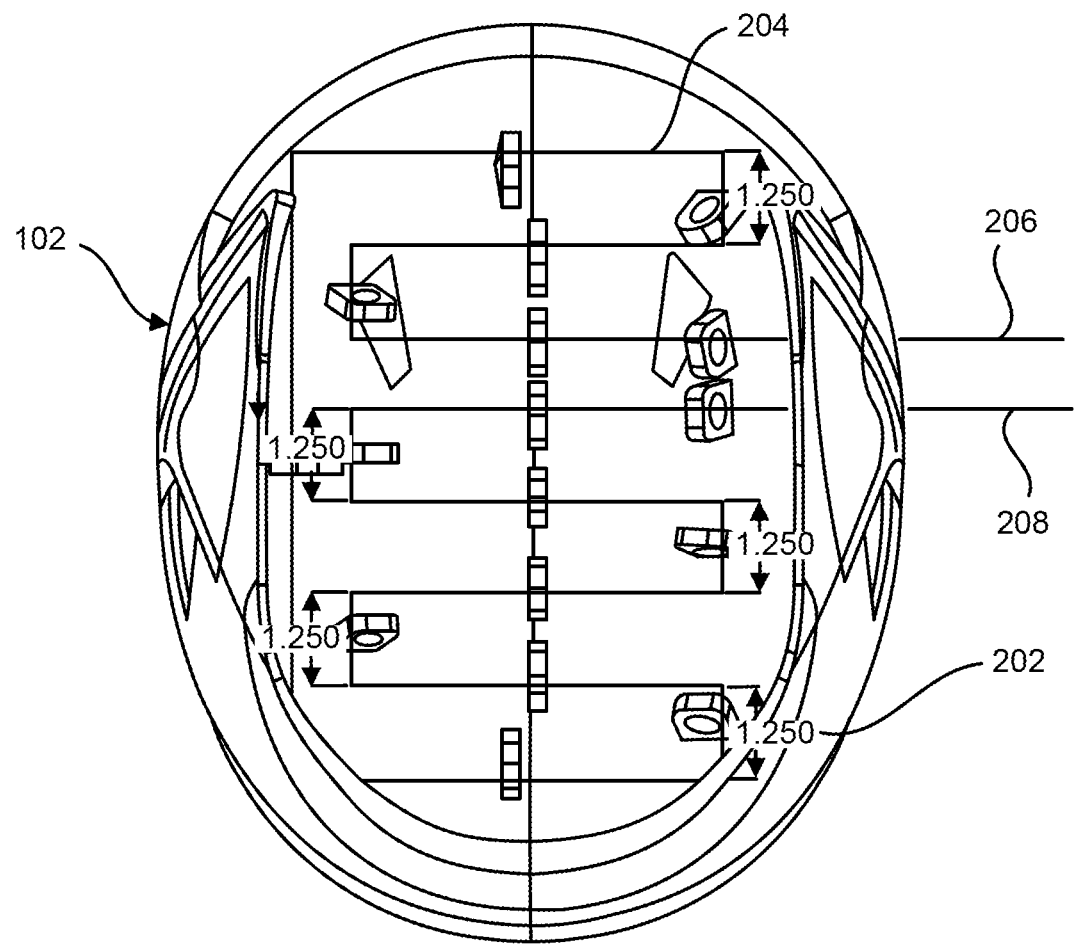
FIG. 4 depicts a bottom view of a cooling cap with a coolant path shown in schematic.

FIG. 4 depicts a perspective bottom view of a cooling cap 102 with a coolant channel 204 depicted. Coolant channel 204 may be capable of containing liquid or gaseous fluids. The fluids may include coolant, water, air, or any other suitable coolant. The cooling channel 204 may be a part of a liquid cooling heat exchanger. The coolant channel 204 may enter the cooling cap 102 through an inlet 206. The coolant channel 204 may exit the cooling cap 102 through an outlet 208. The inlet 206 and outlet 208 may be located anywhere on the exterior of the cooling cap 102. The coolant channel 204 may be held in place by clamps 202. In another embodiment, the coolant channel 204 may be embedded in the cooling cap 102. The coolant channel 204 may be shaped in a variety of patterns within the cooling cap 102. In one embodiment, the coolant channel 204 may be located in a back and forth pattern. In another embodiment, the coolant channel 204 may form a spiral pattern. In another embodiment, the coolant channel 204 may be formed in a pattern to maximize contact with a user's 112 head.

The cooling cap 102 may also be also have temperatures sensors (not shown) embedded in the cooling cap 102 or otherwise part of the system 100. In one embodiment, the temperature sensors may be located on the cooling cap 102, so as to contact the forehead or temple of a user 112. The temperature sensors may be capable of recording temperature of a patient 112 wearing the device. The sensors may be in communication with the cooling control unit 104, electronic device 106, mobile application 110, and network 108.

Figure 5:
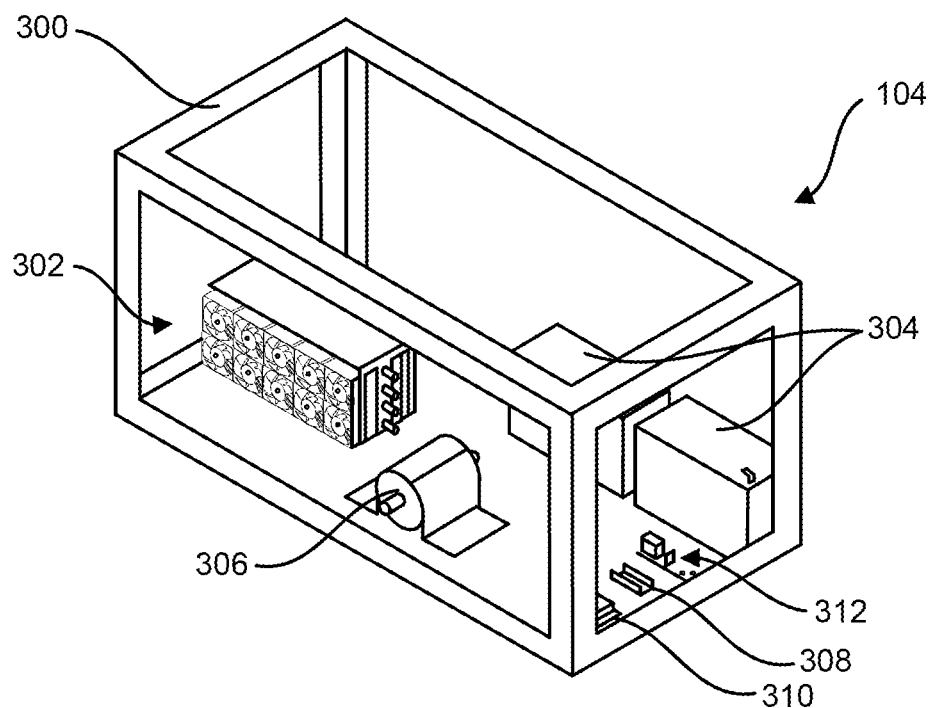
FIG. 5-18 depict a perspective view on the cooling control unit and various components of the cooling control unit.

FIG. 5 depicts a perspective view of one embodiment of a cooling control unit 104. In one embodiment, the cooling control unit 104 unit may have a frame 300, cooling block 302, power source 304, coolant pump 306, controller 308, a converter 310, and a relay. The cooling control unit 104 may have a coolant input channel and coolant output channel (not shown) that are in fluid communication with cooling cap 102. The coolant output channel may provide a coolant to the cooling cap 102. The coolant input channel may receive coolant from the cooling cap 102. The coolant input channel and coolant output channel may be long enough to allow for a patient 112 to move around while wearing the cooling cap 102. In one embodiment, the length of the coolant output channel and coolant input channel may be several feet long. The cooling control unit 104 may be portable and easily moved while tethered to cooling cap 102.

Figure 6:
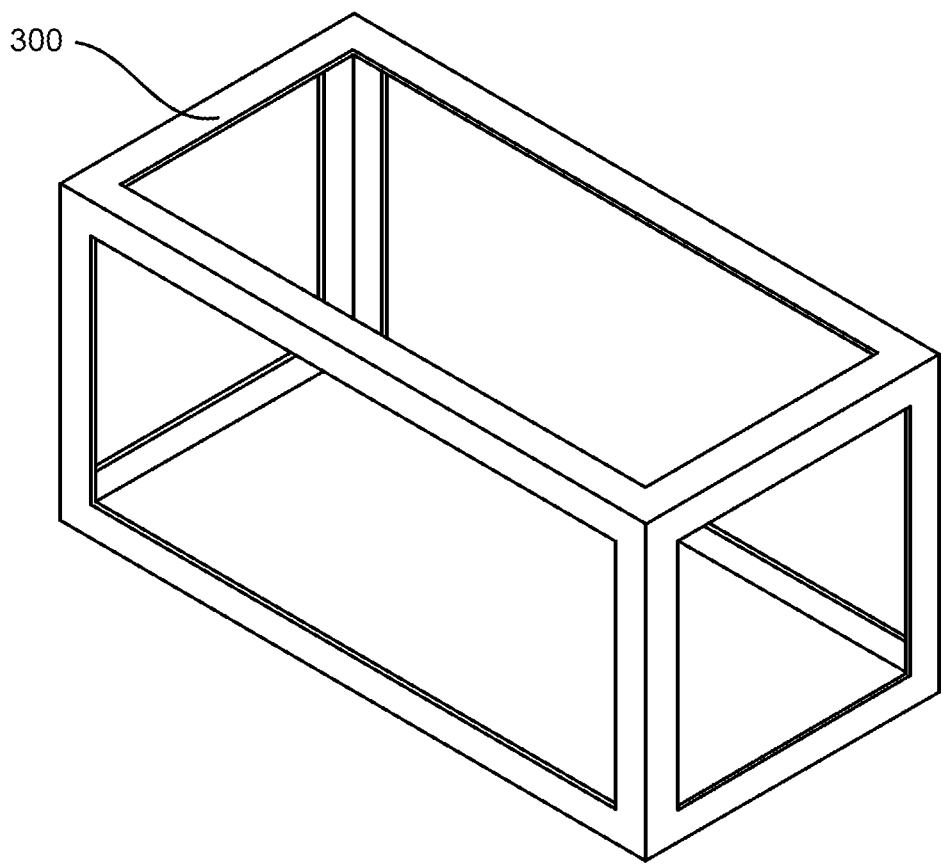

FIG. 6 displays a perspective view of one embodiment of the frame 300 that may house the cooling control unit 104. The frame 300 may be portable and may be various shapes or sizes. In one embodiment, the frame may be rectangular in nature.

Figure 7:
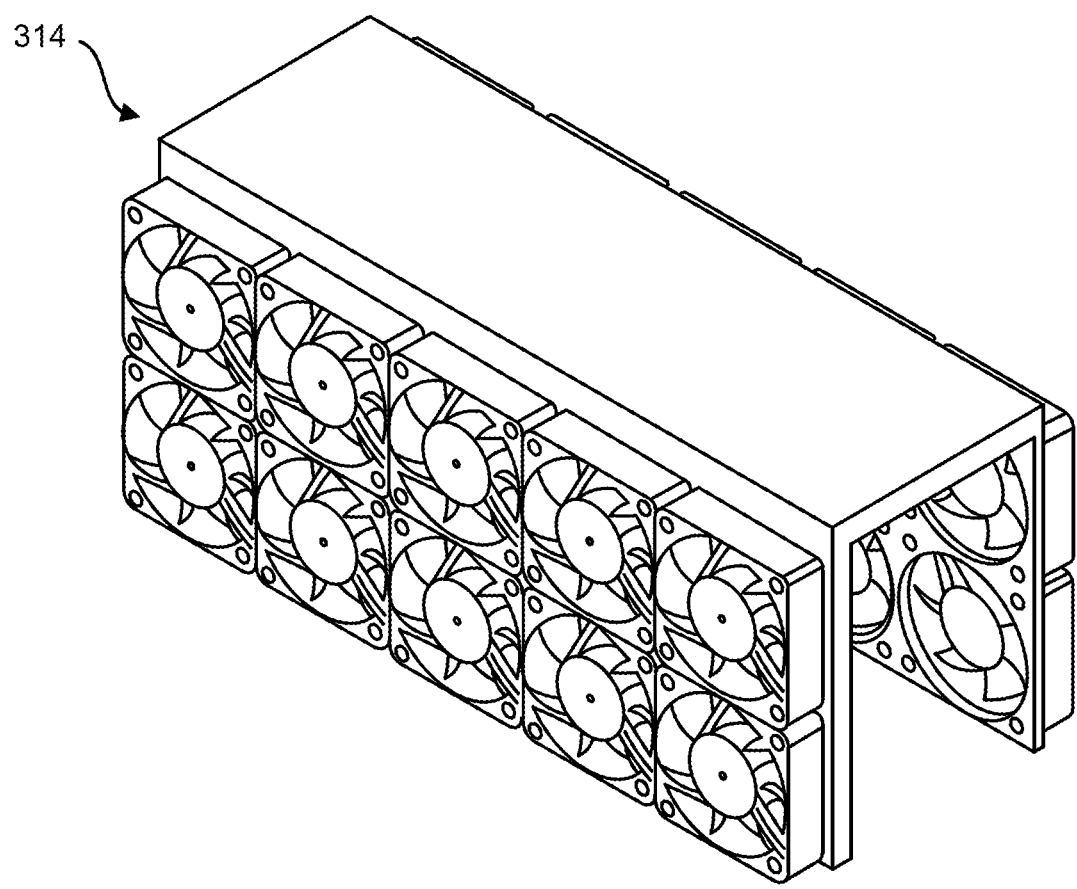
Figure 8:
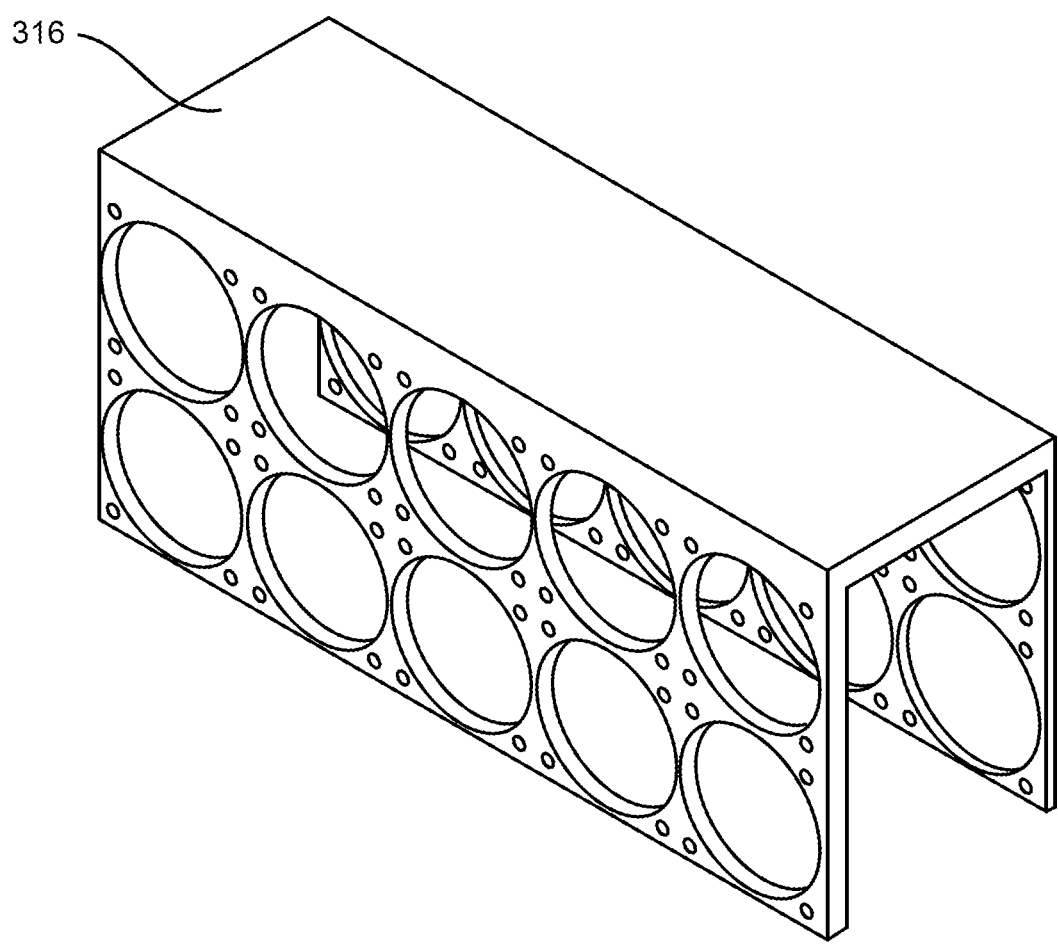
Figure 9:
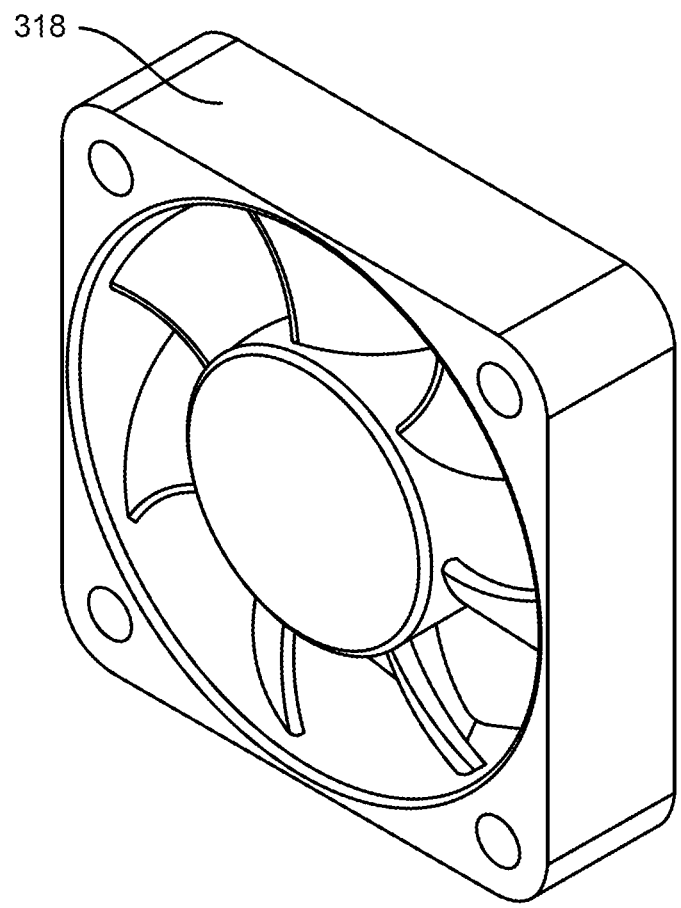
Figure 10:
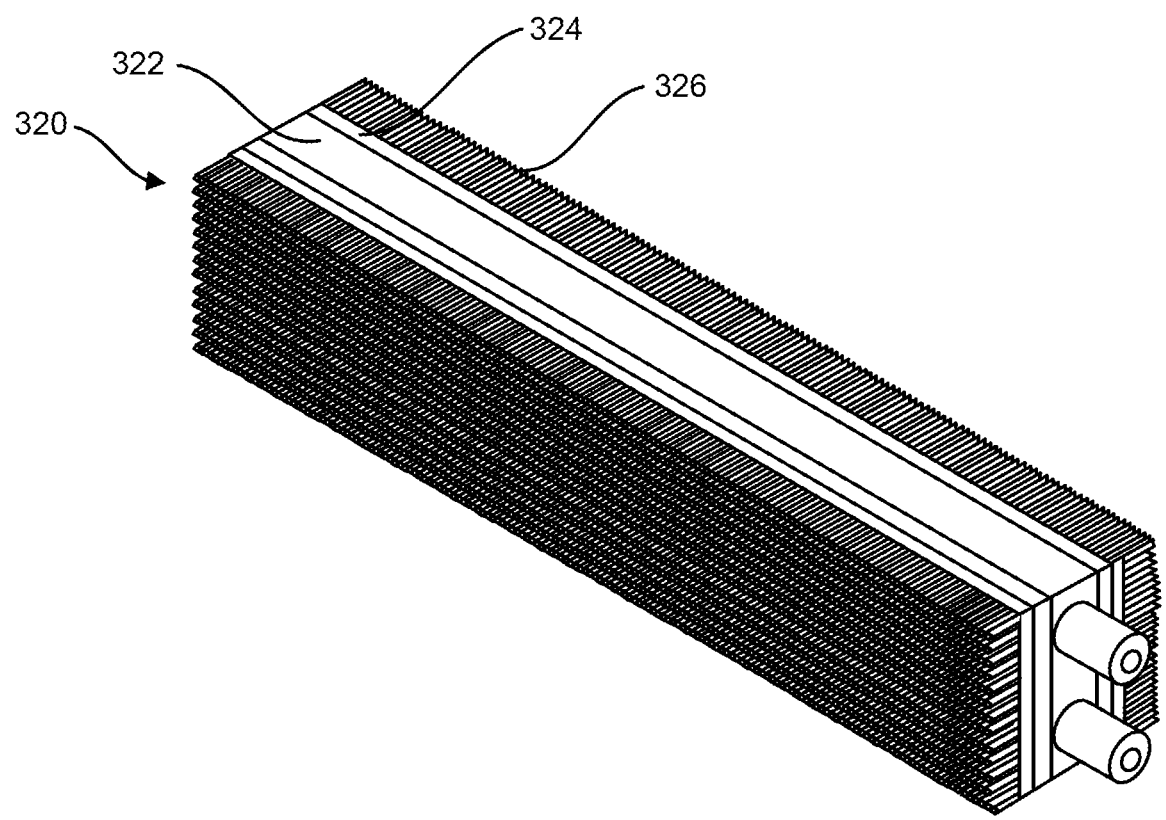
Figure 11:
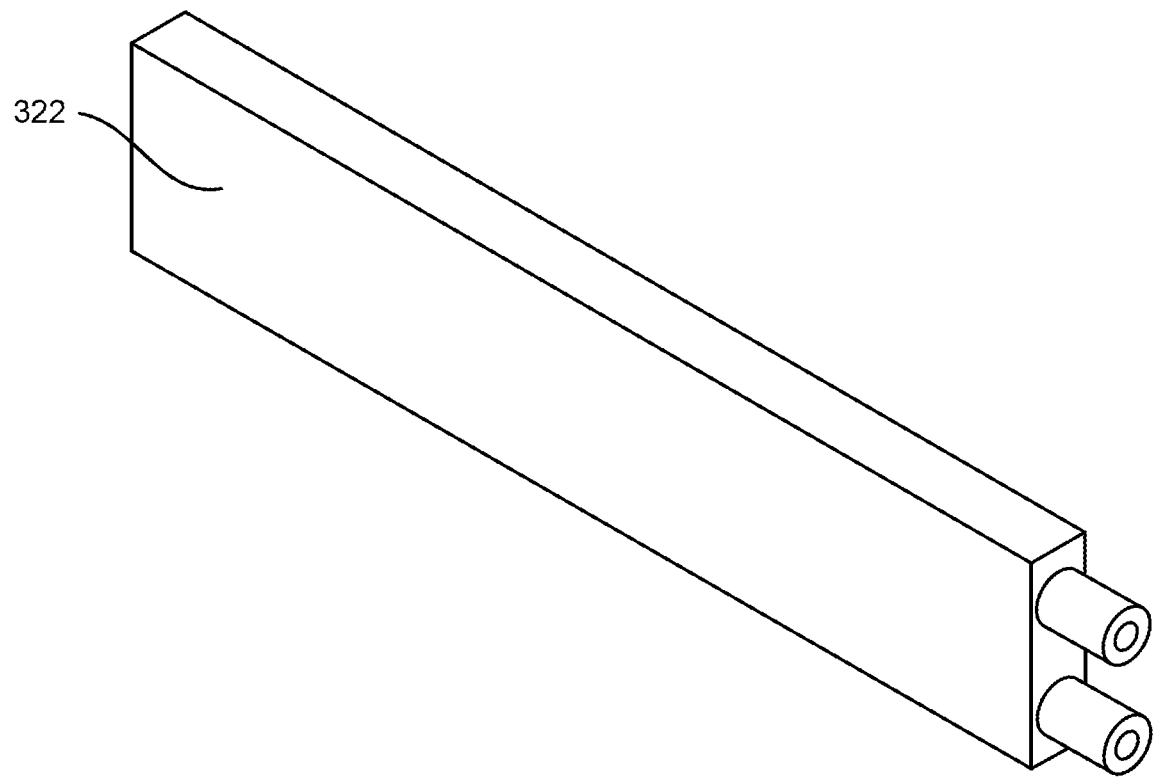
Figure 12:
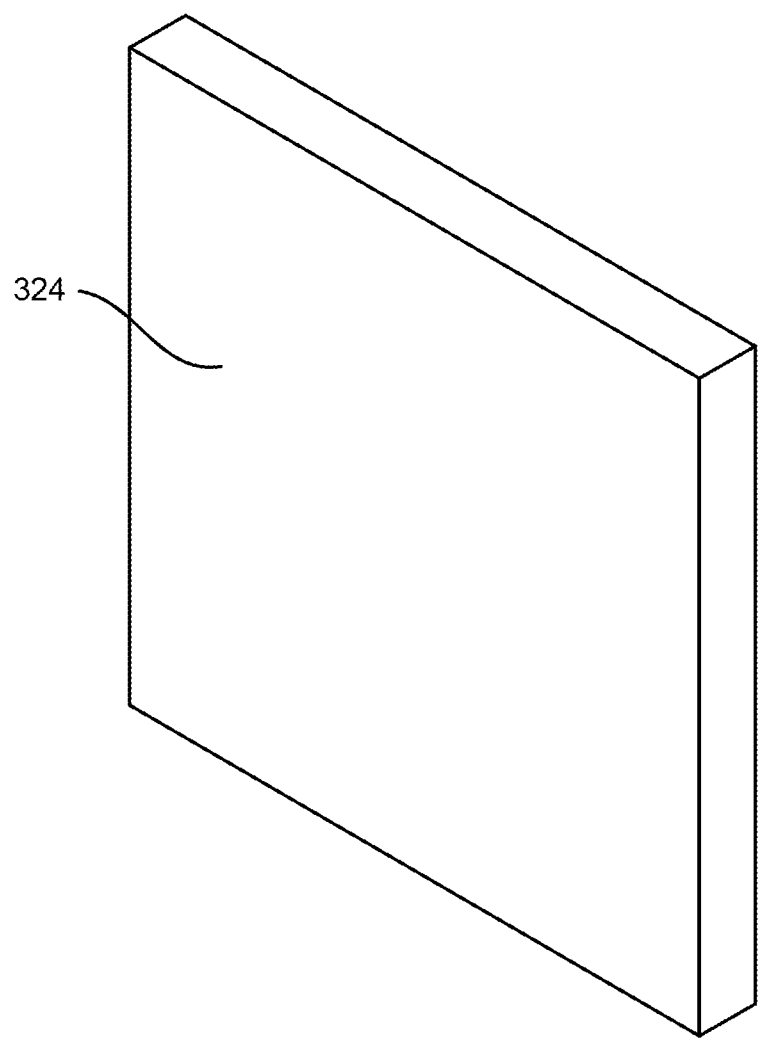
Figure 13:
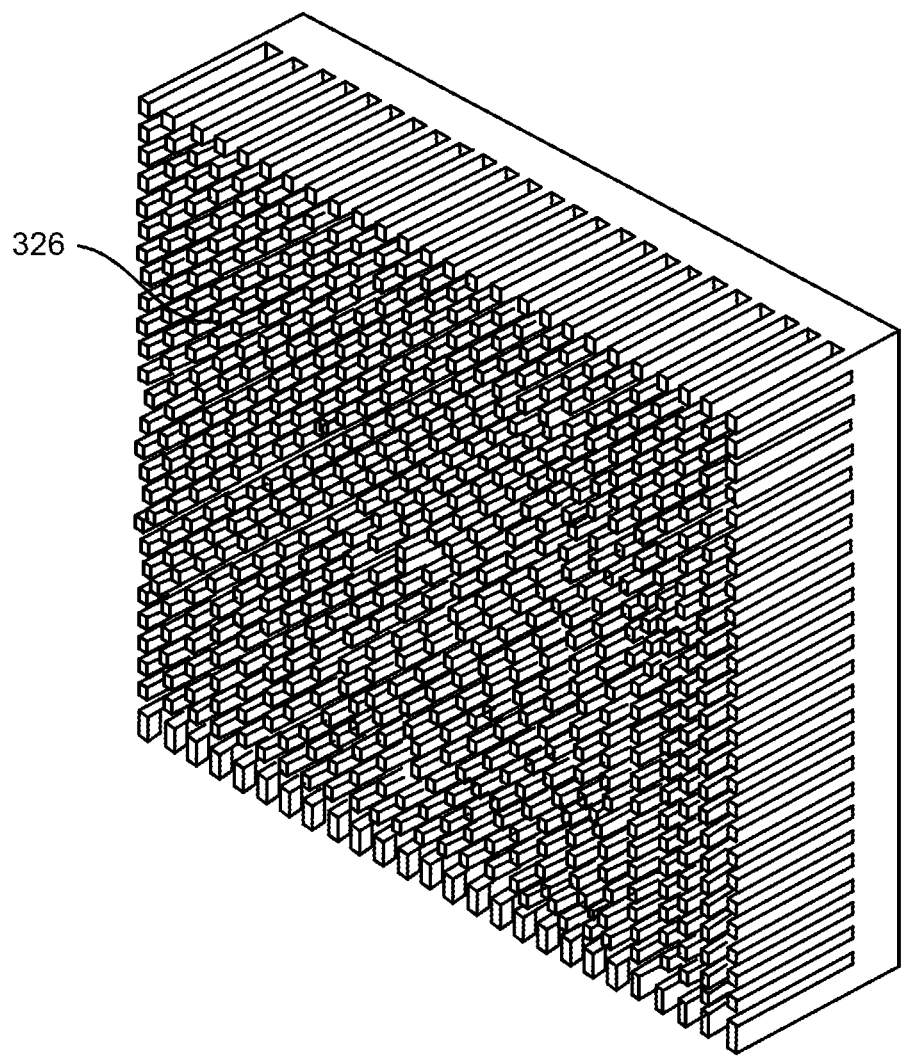

FIGS. 7-13 displays various components of a cooling block 302 located within the cooling control unit 104. FIG. 7 displays a perspective view of a fan unit assembly 314 located within the cooling block or heat exchanger 302 of the cooling control unit 104. In one embodiment, the fan assembly 314 may have twenty fans 318. FIG. 8 displays a perspective view of a bracket 316 used to house fans 318 (shown in FIG. 9). The bracket may be constructed through molding, 3d printing, or machining. FIG. 9 displays a perspective view of a fan utilized in the fan unit assembly 314. FIG. 10 displays a perspective view the main cooling assembly 320 located within the cooling block 302. In one embodiment, the main cooling assembly 320 may include twenty heat sinks 326, twenty thermoelectric coolers 324, and one cooling block 322. FIG. 11 displays a perspective view of a cooling block 322. In one embodiment, the cooling block 322 may be a liquid cooling block. The cooling block 322 may be located in the main cooling assembly 320. FIG. 12 displays a perspective view of a thermoelectric cooler 322 utilized within the main cooling assembly 320. FIG. 13 displays a perspective view of a heat sink 326. The heatsink 326 may be utilized within the cooling assembly 320.

In another embodiment, the cooling control unit 104 may include any viable form of a heat exchanger.

Figure 14:
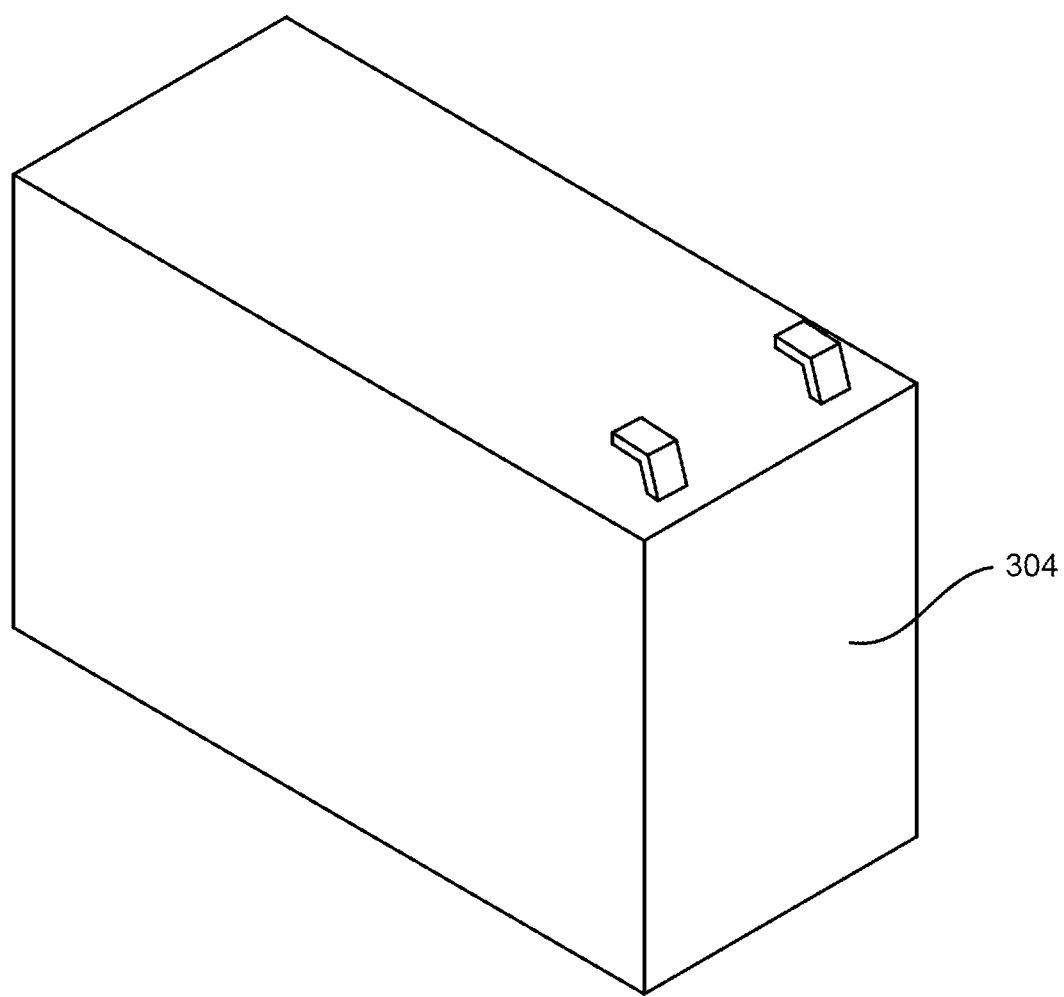

FIG. 14 displays a perspective view of a power source 304 for the cooling control unit 104. The cooling control unit 104 may have one or more power sources 304. In one embodiment, the power source 304 may be a 12-volt battery. In this embodiment, the cooling control unit 104 may have two 12-volt batteries.

Figure 15:
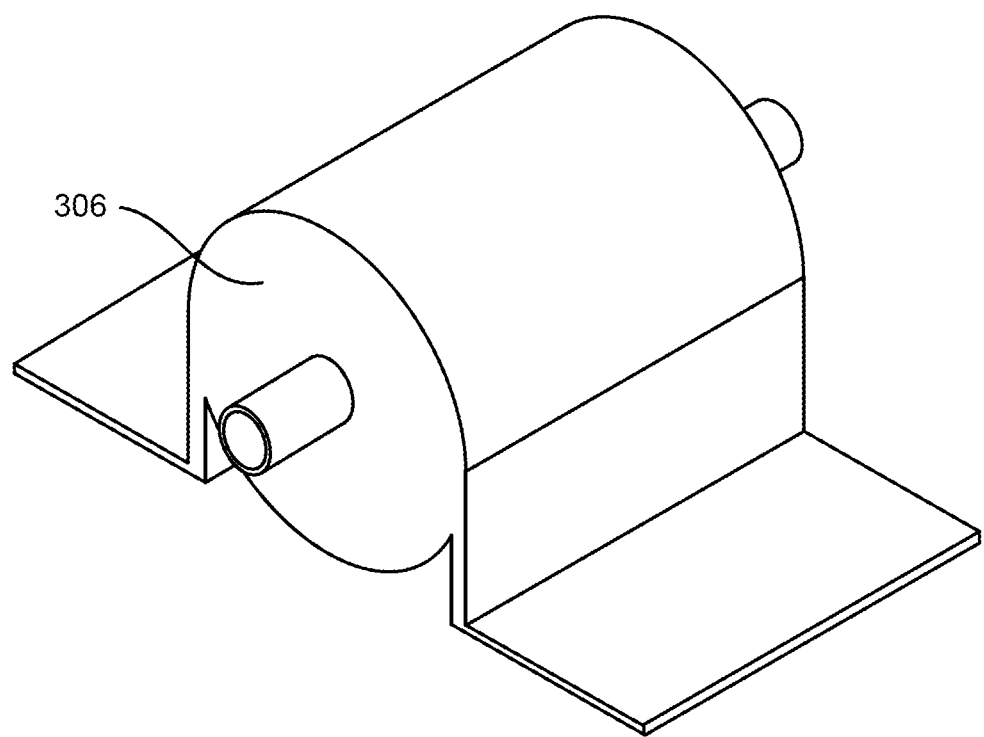

FIG. 15 displays a perspective view of a coolant pump 306. The coolant pump 306 may be utilized to circulate coolant from the cooling control unit 104 through the cooling cap 102.

Figure 16:
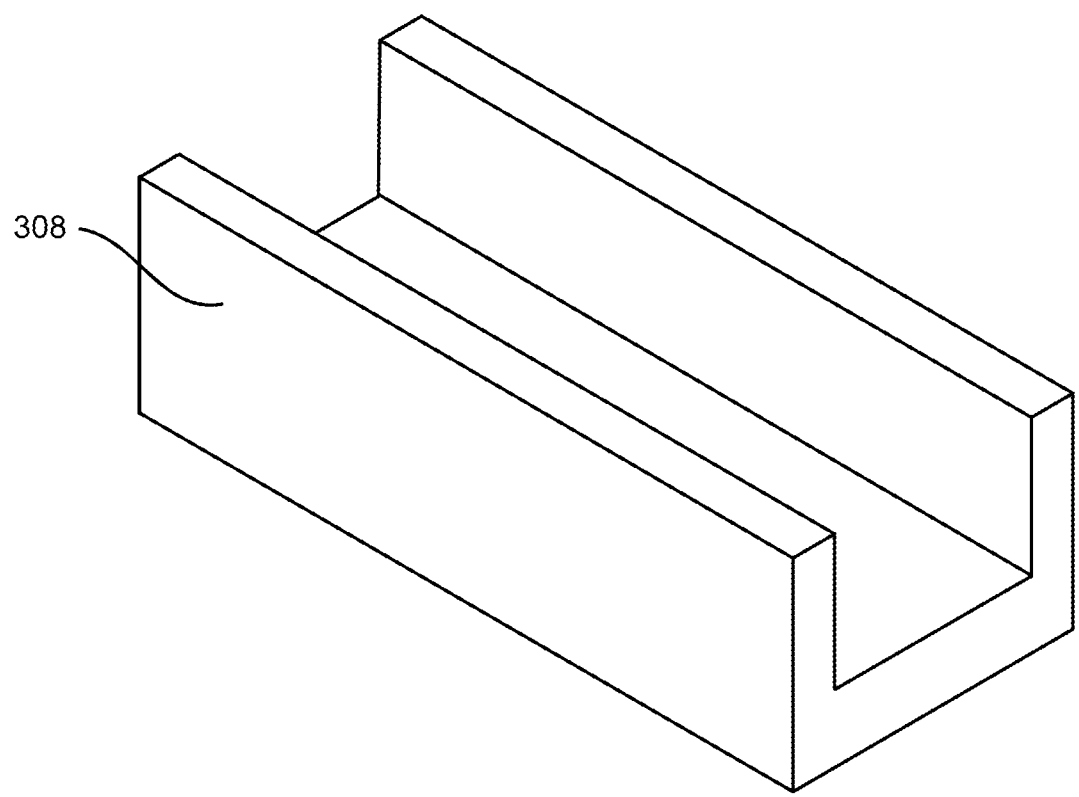

FIG. 16 displays a perspective view of a controller 308. The controller 308 may be responsible for controlling the cooling and pump system within the cooling control unit 104. The controller 308 may receive user input through the mobile application 110. In one embodiment, the controller 308 may be an Arduino Nano.

Figure 17:
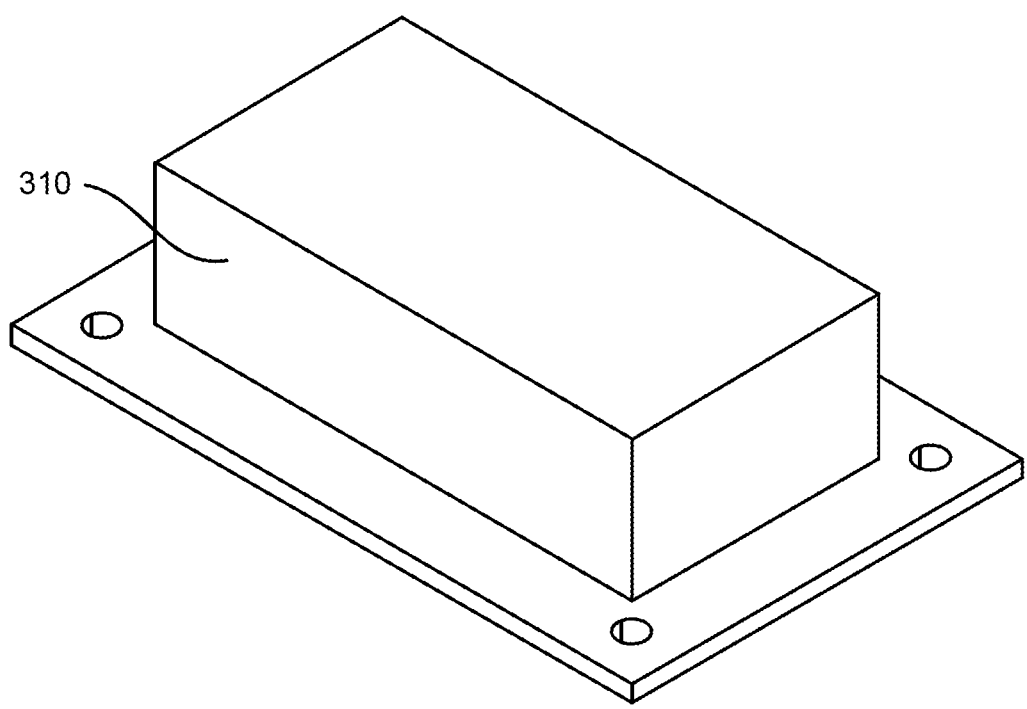

FIG. 17 displays a perspective view of a converter 310. The converter 310 may be responsible for converting high voltage to lower voltage for the cooling control unit 104.

Figure 18:
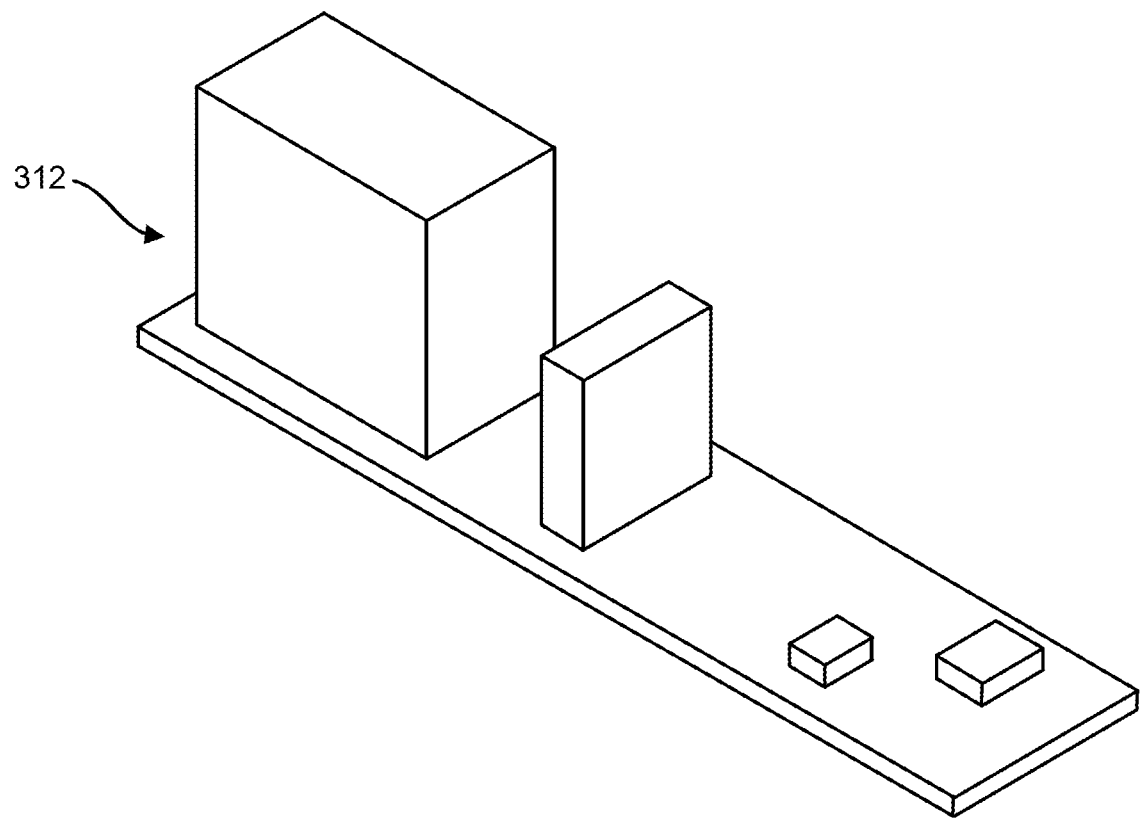

FIG. 18 displays a perspective view of relay 312 utilized by the cooling control unit 104.

Figure 19:
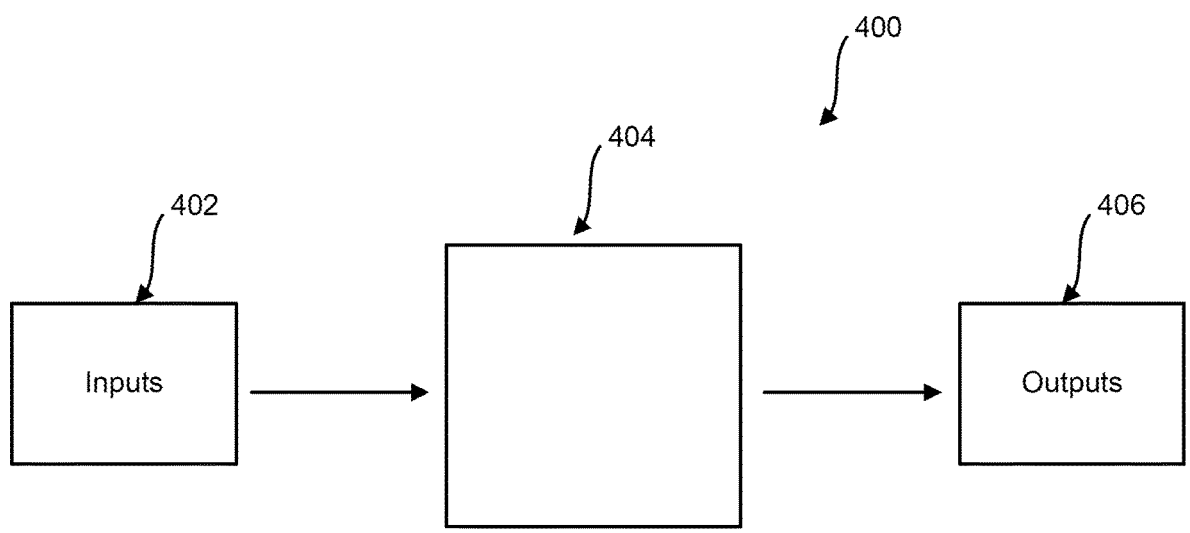
FIG. 19 is a block illustration of a processor, according to an example of the present disclosure.

FIG. 19 is a schematic representative of a processor system 400, according to an example of the present disclosure. Flowchart 400, has inputs 402 of GSC score provided by mobile application 110 and temperature from cooling cap 102. Processor 404 will then determine whether patient 112 requires use of a coolant cap 102. Processor 404 will provide an output 406 determining that patient 112 should utilize coolant cap 102 or should not utilize coolant cap 102. In one embodiment, If the output 406 determines that the coolant cap 102 should not be utilized, the coolant cap 102 may be electronically restricted from turning on and delivering coolant.

Figure 20:
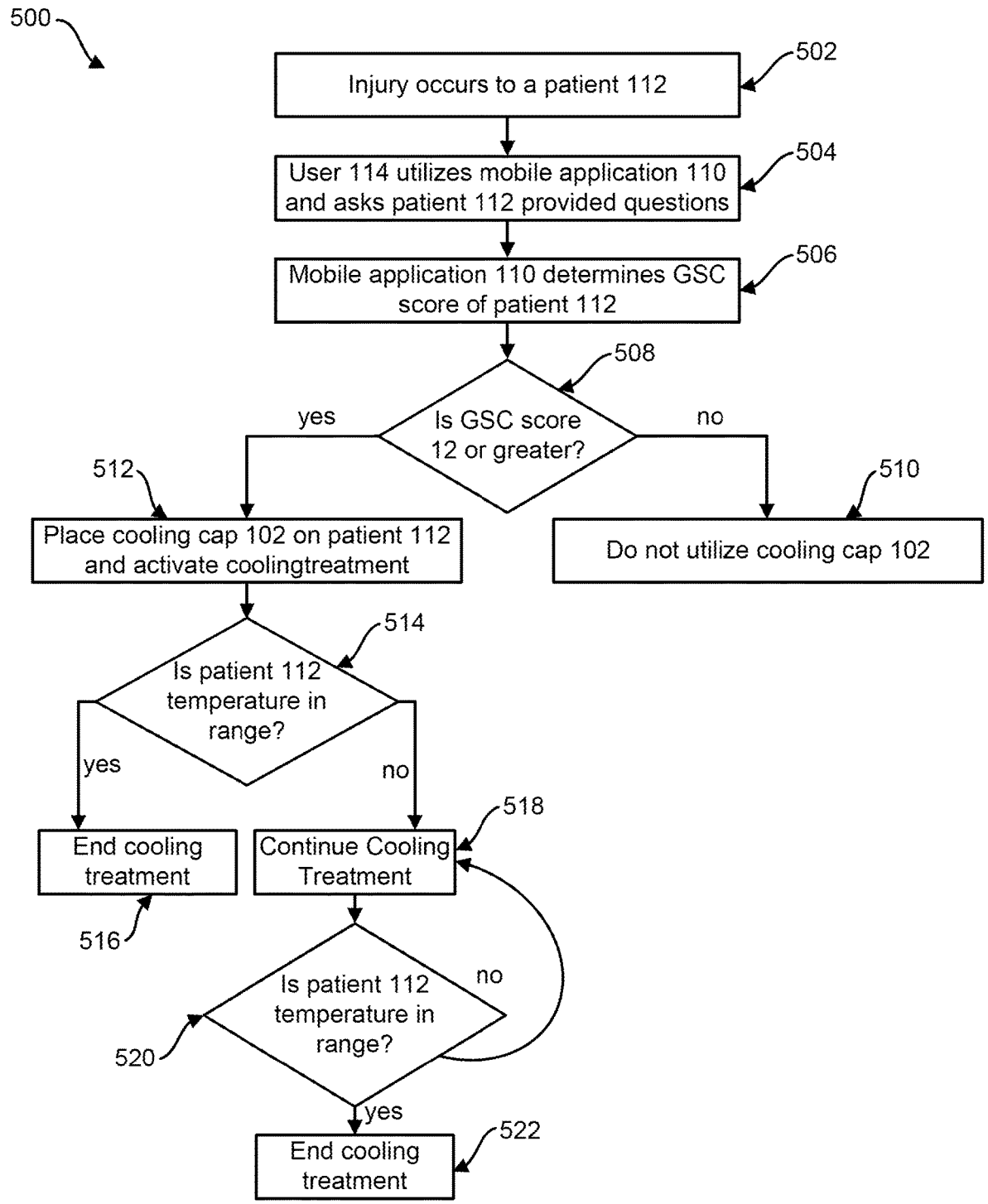
FIG. 20 is a flowchart of an exemplary cooling system method, according to another example of the present disclosure.

FIG. 20 is a flowchart of an exemplary cooling system method, according to another example of the present disclosure. Flowchart 500 may provide an exemplary method for the cooling system 100. Step 502 includes a patient 112 sustaining a potential TBI. At step 504, a different individual 114, such as an athletic trainer, or the patient 112 may open the mobile application 110. The individual 114 may then ask the injured patient 112 a series of questions provided by the mobile application 110. The individual 114 may then enter the answers to the questions into the mobile application 110. In one embodiment, step 504 may be performed within ten minutes of an event causing the traumatic brain injury .At step 506, the mobile application 110 may then determine a GSC score for a patient 112. At step 508, the mobile application 110 may determine whether the GSC score is 12 or greater. At step 510, if the patient's 112 GSC score is 11 or under, the mobile application 110 may instruct the user to not put on the cooling cap 102. The mobile application 110 may still instruct the patient 112 to seek further medical evaluations. If the patent's 112 GSC score is 12 or greater, the mobile application may instruct that the cooling cap 102 be placed on the patient 112 head in step 512. The cooling cap 102 may only work if a score of 12 or higher is recorded by the mobile application 110. In one embodiment, the mobile application 110 may provide an authentication code needed to activate the cooling cap 102 only after a GSC score of 12 or greater has been determined. In another embodiment, the cooling cap 102 may be electronically disabled from providing coolant until a score of 12 or higher is determined by the mobile application 110. In step 512, the cooling cap 102 be activated. This may lead to coolant being administered to the coolant cap 102 from the coolant control unit 104. The coolant cap may then be used to perform selective cerebral hypothermia to potentially limit the extent of a brain injury of the patient 112. Step 512, may occur for a set period of time. In another embodiment step 512 may be instantaneous and the system may immediately move to step 514. In another embodiment, step 512 may occur for fifteen minutes and then the system may move to step 514. In step 514, the patient's 112 temperature may be analyzed. If the patient's 112 temperature is below a predetermined threshold value, the system may end the cooling treatment in step 516. If treatment is ended, patient 112 may be instructed to remove cooling cap 102. After cooling treatment has ended, the patient 112 may still be instructed to answer questions from the mobile application 110 in the following days or weeks. This data may be recorded within the system 100. If patient's 112 temperature is not below a predetermined threshold value, the cooling treatment may continue in step 518. After select periods of time, the patient's temperature will be reanalyzed in step 520. If temperature has moved below the predetermined threshold value, the cooling treatment may end in step 522. If the temperature is still not below the predetermined threshold value, the system may move back to step 518 and continue the cooling treatment. The system may also have a maximum time period for providing a cooling treatment. In one embodiment, the maximum time period to provide a cooling treatment may be forty five minutes. Once the maximum time period of cooling treatment has occurred, the cooling treatment may end regardless of the patient's 112 temperature. In one embodiment, after the cooling treatment ends at step 522, the cooling cap 102 may stay on the patients 112 head for a certain period of time to continue to record information of the patient 112.

What is claimed is:

1. A method, consisting essentially of:
   receiving diagnostic information, using a mobile application, relating to a potential traumatic brain injury of a person, wherein receiving diagnostic information includes receiving answers to a questionnaire relating to the person, wherein the questionnaire includes a series of questions relating to the potential traumatic brain injury;
   based on the received diagnostic information, determining a Glascow Coma Scale for the person;
   upon determining that the Glascow Coma Scale is above a threshold value, instructing use of a cooling system to manage a temperature of the person's head, wherein the cooling system includes:
   1) an insulated cap having one or more fluid conduits extending through the cap, wherein the cap is a helmet;
   2) a cooling control unit, wherein the cooling control unit include a housing, a cooling assembly, a power source, a coolant pump configured to circulate coolant through the cooling system, a controller configured to control the coolant pump, and a converter, wherein the control unit is configured to prevent use of the cooling system when the determined Glascow Coma Scale is below the threshold value;
   3) wherein the cooling assembly includes one or more cooling blocks through which coolant is configured to flow, a heat sink, and a thermoelectric cooler, wherein the cooler assembly is configured to remove heat from coolant flowing therethrough;

4) a fluid line disposed between the cap and the cooling unit that tethers to cap and the cooling unit to one another;

5) one or more temperatures sensors configured to measure a temperature of the person's head, wherein the one or more temperature sensors are coupled to the cap so as to contact a forehead or temple of the person when the cap is worn;

the method further comprising:

after the cap has been placed on a head of the person, operating the cooling system to flow liquid coolant through the cooling system to perform selective cerebral hypothermia to limit an extent of brain injury to the person;

after the one or more temperature sensors have been placed in contact with the forehead or temple of the person, receiving measured temperature from the one or more temperature sensors;

when the received measured temperature is below a low temperature threshold, ceasing the flow of coolant through cooling system;

after cessation of use of the cooling system, sending an instruction to submit answers to additional questions, through the mobile application, after lapse of at least one day from cessation of use of the cooling system, wherein the additional questions relate to the potential traumatic brain injury of the person; and after lapse of at least one day from cessation of use of the cooling system, receiving the answers to the additional questions through the mobile application.

2. A method, comprising:

receiving diagnostic information, using a mobile application, relating to a potential traumatic brain injury of a person, wherein receiving diagnostic information includes receiving answers to a questionnaire relating to the person, wherein the questionnaire includes a series of questions relating to the potential traumatic brain injury;

based on the received diagnostic information, determining a Glascow Coma Scale for the person;

upon determining that the Glascow Coma Scale is above a threshold value, instructing use of a cooling system to manage a temperature of the person's head, wherein the cooling system includes:

1) an insulated cap having one or more fluid conduits extending through the cap;

2) a cooling control unit, wherein the cooling control unit include a housing, a cooling assembly, a power source, a coolant pump configured to circulate coolant through the cooling system, a controller configured to control the coolant pump, and a converter, 3) wherein the cooling assembly includes one or more cooling blocks through which coolant is configured to flow, a heat sink, and a thermoelectric cooler, wherein the cooler assembly is configured to remove heat from coolant flowing therethrough;

4) a fluid line disposed between the cap and the cooling unit that tethers to cap and the cooling unit to one another;

5) one or more temperature sensors configured to measure a temperature of the person's head, wherein the one or more temperature sensors are coupled to the cap so as to contact a forehead or temple of the person when the cap is worn;

the method further comprising:

after the cap has been placed on a head of the person, operating the cooling system to flow liquid coolant through the cooling system to perform selective cerebral hypothermia to limit an extent of brain injury to the person;

after the one or more temperature sensors have been placed in contact with the forehead or temple of the person, receiving measured temperature from the one or more temperature sensors;

when the received measured temperature is below a low temperature threshold, ceasing the flow of coolant through cooling system;

after cessation of use of the cooling system, sending an instruction to submit answers to additional questions, through the mobile application, after lapse of at least one day from cessation of use of the cooling system, wherein the additional questions relate to the potential traumatic brain injury of the person; and after lapse of at least one day from cessation of use of the cooling system, receiving the answers to the additional questions through the mobile application.

3. The method of claim 2, wherein the cap is a helmet.

4. The method of claim 3, wherein the one or more fluid conduits are embedded within the cap.

5. The method of claim 2, wherein the control unit is configured to prevent use of the cooling system when the determined Glascow Coma Scale is below the threshold.

6. The method of claim 2, wherein, when the measure temperature rises above the low temperature threshold, re-initiating a flow of coolant through the cooling system to withdraw heat from the head of the person.

7. The method of claim 2, wherein the low temperature threshold is 35 degrees Celsius.

8. The method of claim 2, wherein receiving the diagnostic information occurs within ten minutes of an event causing the traumatic brain injury.

9. The method of claim 2, further including receiving measured temperature of the person's head for at least ten minutes after cessation of flow of coolant through the coolant system.

10. The method of claim 2, wherein:

the cap is a helmet;

the one or more fluid conduits are embedded within the cap;

the control unit is configured to prevent use of the cooling system when the determined Glascow Coma Scale is below the threshold;

when the measure temperature rises above the low temperature threshold, re-initiating a flow of coolant through the cooling system to withdraw heat from the head of the person;

the low temperature threshold is 35 degrees Celsius;

receiving the diagnostic information occurs within ten minutes of an event causing the traumatic brain injury; and receiving measured temperature of the person's head for at least ten minutes after cessation of flow of coolant through the coolant system.

* * * * *